United States Patent
Foulkes et al.

(10) Patent No.: US 6,977,152 B2
(45) Date of Patent: Dec. 20, 2005

(54) BIOLOGICAL ASSAYS USING CODED RNA REPORTERS

(75) Inventors: J. Gordon Foulkes, Encinitas, CA (US); Oren E. Beske, Belmont, CA (US)

(73) Assignee: Virtual Arrays, Inc., Sunnyvale, CA (US)

( * ) Notice: Subject to any disclaimer, the term of this patent is extended or adjusted under 35 U.S.C. 154(b) by 584 days.

(21) Appl. No.: 10/238,914

(22) Filed: Sep. 9, 2002

(65) Prior Publication Data

US 2003/0082608 A1    May 1, 2003

Related U.S. Application Data

(60) Provisional application No. 60/318,156, filed on Sep. 7, 2001.

(51) Int. Cl.[7] .................... C12Q 1/68; C07H 21/02; C07H 21/04
(52) U.S. Cl. .................... 435/6; 536/23.1; 536/24.3
(58) Field of Search .................... 435/6; 536/23.1, 536/24.3

(56) References Cited

U.S. PATENT DOCUMENTS

| | | |
|---|---|---|
| 5,912,132 A | 6/1999 | Brann |
| 5,985,214 A | 11/1999 | Stylli et al. |
| 6,060,272 A | 5/2000 | Li et al. |
| 6,063,596 A | 5/2000 | Lal et al. |
| 6,291,177 B1 | 9/2001 | Madden et al. |
| 6,453,242 B1 | 9/2002 | Eisenberg et al. |
| 6,518,035 B1 * | 2/2003 | Ashby et al. .................... 435/18 |
| 6,770,446 B1 * | 8/2004 | Young et al. .................... 435/7.1 |

FOREIGN PATENT DOCUMENTS

| | | |
|---|---|---|
| WO | WO 00/63419 | 10/2000 |
| WO | WO 02/37944 | 5/2002 |

OTHER PUBLICATIONS

*Bind Every Sequence*, Sangamo BioSciences, Inc., *Chemistry & Biology*, vol. 6, pp. R281-R283, Oct. 1999.
*Transcription Control: Imprinting Insulation*, Wolffe, *Current Biology*, vol. 10, pp. R463-R465, 2000.
*Engineering Polydactyl Zinc-Finger Transcription Factors*, Beerli et al., *Nature Biotechnology*, vol. 20, pp. 135-141, Feb. 2002.
*Regulatable Gene Therapy*, Habeck, *Drug Discovery Today*, vol. 7, No. 17, pp. 888-889, Sep. 2002.
*Biotechnologies and Therapeutics: Chromatin as a Target*, Reik et al., *Current Opinion in Genetics & Development*, vol. 12, pp. 233-241, 2002.

* cited by examiner

Primary Examiner—Ethan Whisenant
(74) Attorney, Agent, or Firm—Kolisch Hartwell, P.C.

(57) ABSTRACT

Systems for multiplexed analysis of gene expression using coded RNA reporters. The coded RNA reporters are expressed from a library of reporter genes, with each reporter gene directing expression of a distinguishable coded RNA reporter. Each RNA reporter thus reports activity of a corresponding reporter gene. The distinguishable reporter RNA species allow otherwise similar reporter genes to be functionally linked to different effectors within a cell reporter library. Multiplexed analysis of reporter gene activity is carried out by measuring the level of each RNA reporter within the cell reporter library, thus providing an ability to analyze the effect of a biological modulator on many effectors.

22 Claims, 1 Drawing Sheet

BIOLOGICAL ASSAYS USING CODED RNA REPORTERS

CROSS-REFERENCES TO PRIORITY APPLICATIONS

This application claims the benefit under 35 U.S.C. § 119(e) of U.S. Provisional Patent Application Ser. No. 60/318,156, filed Sep. 7, 2001, which is incorporated herein by reference in its entirety for all purposes.

CROSS-REFERENCES TO ADDITIONAL MATERIALS

This application incorporates by reference in their entirety for all purposes the following U.S. patent applications: Ser. No. 09/549,970, filed Apr. 14, 2000; Ser. No. 09/694,077, filed Oct. 19, 2000; and Ser. No. 10/120,900, filed Apr. 10, 2002.

This application also incorporates by reference in their entirety for all purposes the following U.S. provisional patent applications: Ser. No. 60/343,682, filed Oct. 26, 2001; Ser. No. 60/343,685, filed Oct. 26, 2001; Ser. No. 60/344,482, filed Oct. 26, 2001; Ser. No. 60/344,483, filed Oct. 26, 2001; Ser. No. 60/348,025, filed Oct. 26, 2001; Ser. No. 60/348,027, filed Oct. 26, 2001; Ser. No. 60/359,207, filed Feb. 21, 2002; Ser. No. 60/362,001, filed Mar. 5, 2002; Ser. No. 60/362,055, filed Mar. 5, 2002; Ser. No. 60/362,238, filed Mar. 5, 2002; Ser. No. 60/370,313, filed Apr. 4, 2002; Ser. No. 60/383,091, filed May 23, 2002; and Ser. No. 60/383,092, filed May 23, 2002.

FIELD OF THE INVENTION

The invention relates to analysis of gene expression in biological systems. More particularly, the invention relates to multiplexed analysis of gene expression in biological systems using RNA reporters.

BACKGROUND

Reporter genes are used in studies of biological systems to facilitate measurement of gene activity. Generally, reporter genes are exogenous gene sequences that are introduced into cells using techniques such as transfection. Reporter genes may include an expressible region and a regulatory region. The expressible region generally encodes a readily quantifiable protein or protein activity, for example, an enzyme such as chloramphenicol acetyltransferase or beta-galactosidase, or a fluorescent protein, such as green fluorescent protein. The regulatory region generally regulates expression of the expressible region and typically includes a control element or set of control elements that mimics regulation of an endogenous gene or set of genes.

Reporter genes may be used as targets to analyze the activity of specific effector proteins. For example, cells may be engineered to express a specific receptor of interest and to include a target reporter gene that responds to the receptor. In this way, the activity of the receptor may be assessed by monitoring the presence, absence, level, and/or characteristics of the reporter gene. With this system, the activity of the receptor on the target reporter gene may be analyzed in the presence of receptor modulators to determine the ability of each modulator to function as an agonist or antagonist of receptor activity. Using this approach, natural or synthetic, activating or inhibiting ligands for the receptor may be identified in drug screens, thus providing potential candidate drugs for in vivo use.

Unfortunately, the number of known or candidate receptor proteins that has been molecularly cloned has far outstripped the ability of these methods to identify modulators of these receptor proteins by studying one receptor at a time. Thus, a multiplexed system for analyzing receptor proteins in modulator screens would greatly facilitate the identification of receptor agonists and antagonists. To determine the effects of a particular compound on multiple receptors in a single well, researchers would have to engineer a specific reporter for each receptor, introduce the engineered reporters into cells, expose the cells to the compound, and quantify the amount of each reporter. The activation of receptor #1 would result in the expression of reporter #1, the activation of receptor #2 would result in the expression of reporter #2, and so on. Therefore, the effects of a single compound on multiple receptors could be determined by quantifying the amount of each reporter.

Despite the need for multiplexed receptor analysis, current reporter genes that rely on quantification of an expressed reporter protein may have limited utility in multiplexed screens. For example, the ability to distinguish and quantify efficiently a large number of reporter proteins within a single container is impractical or impossible with current technology. For example, optical methods may be limited in their ability accurately to resolve signals produced directly or indirectly by more than two or three reporter proteins. In the case of enzyme reporter proteins, distinct enzymes may require different assay conditions, distinct substrates, and thus separate assays for each enzyme activity. Due to these inadequacies, there is a need for a reporter gene system that allows multiplexed analysis of larger sets of target genes and effector proteins.

SUMMARY OF THE INVENTION

The invention provides systems for multiplexed analysis of gene expression in biological systems using RNA reporters.

DETAILED DESCRIPTION

Figure 1:
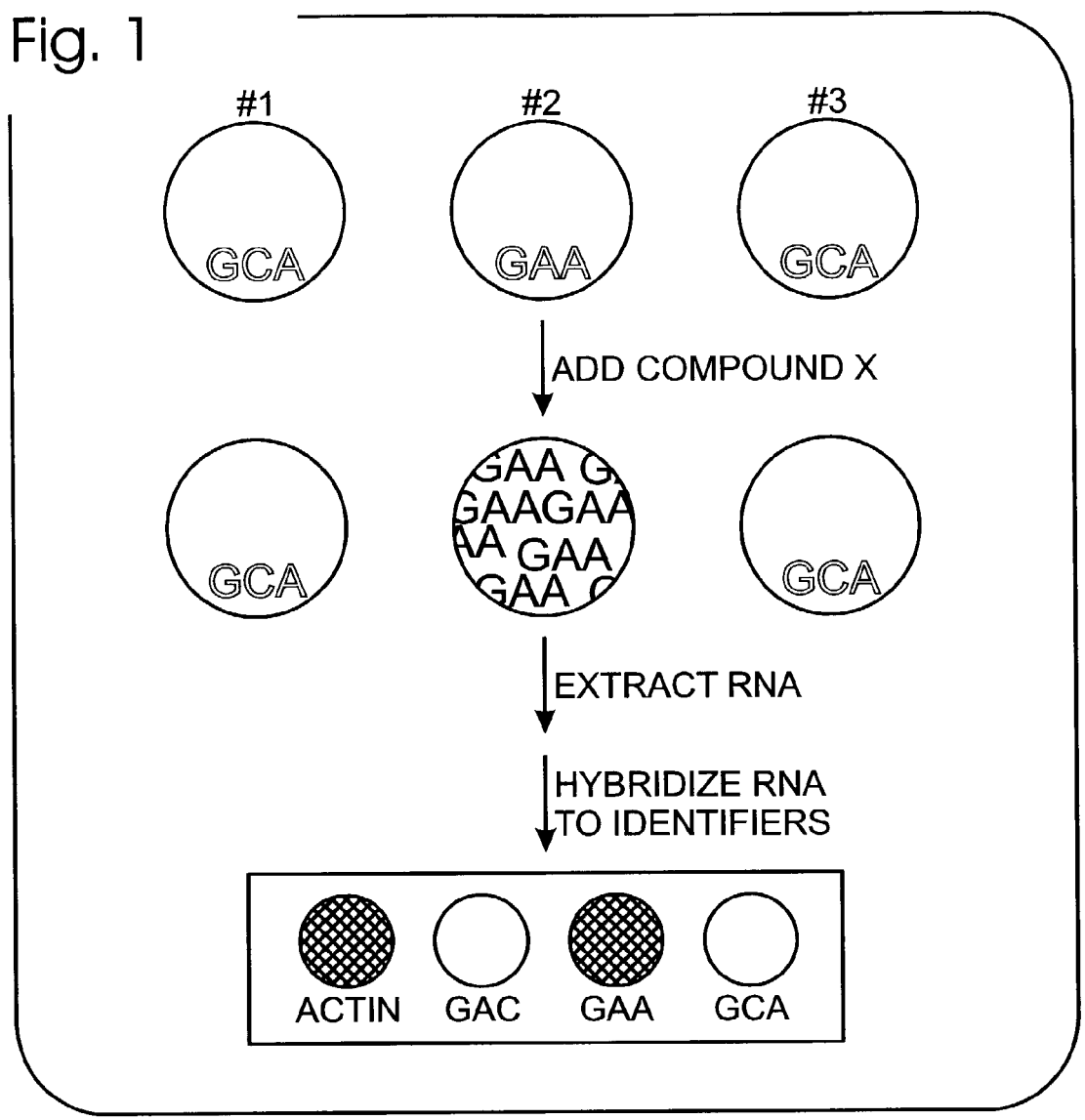
FIG. 1 is a schematic view of multiplexed analysis using RNA reporters to determine a modulator's effect on plural receptors, in accordance with aspects of the invention.

The invention provides systems for multiplexed analysis of gene expression in biological systems using RNA reporters. The systems provided by the invention may include methods for making and using a library of reporter genes that express distinguishable, coded RNA reporters. Each reporter gene in the library may have a common or distinct regulatory region. Furthermore, each library member may be introduced into, and reside in, a distinct reporter cell population, or the library may be introduced en masse into a reporter cell population. The systems provided by the invention also may include kits comprising libraries of reporter genes, typically in the form of DNA plasmids, and/or libraries of cells transfected with members of the libraries of reporter genes. In some embodiments, the kits also may include components of a readout mechanism, such as chips, particles, or other elements of a positional or nonpositional array.

Each distinct reporter cell population may acquire distinctiveness, in part, through introduction of at least one exogenously expressed effector protein. The effector protein may directly or indirectly affect expression from the resident reporter gene(s). Each RNA reporter thus reports activity of a distinguishable reporter gene. The distinguishable reporter RNA species may allow otherwise similar reporter genes to be functionally linked to different effectors within a cell reporter library. By producing and combining distinct reporter cell populations with distinguishable reporter genes (and optionally distinct effectors), a reporter cell library may be generated. The reporter cell library may be used to effect multiplexed analysis of modulators, for example, drug candidates in a drug screen, on each reporter cell population in the reporter cell library. As a result, the activity of a modulator on plural effectors, reporter gene targets, and/or cell types may be measured through multiplexed analysis of RNA reporter levels from the reporter cell library. This multiplexed analysis of the reporter cell library may reduce the time, effort, and cost necessary for identifying effective modulators in drug screens.

The RNA reporter systems provided by the invention may have one or more advantages over current reporter systems. For example, many current reporter systems are limited by the fact that their measurement depends on functional protein activity for accurate measurement, such that positive assay results may be undetectable even if the RNA reporter is produced and translated if the expressed protein is not functional. However, by assaying mRNA levels rather than functional protein activity, this limitation may be surpassed, because only a transcription product is required. Moreover, by using RNA reporters rather than proteins, the activity of a receptor may be accurately determined by standard RNA detection techniques rather than functional protein assays. RNA reporters also are more flexible than protein reporters, because RNA reporters generally do not require open reading frames. Thus, the sequence of the RNA reporter may be randomized without regard for canonical translation requirements. When the receptor is activated, the RNA-reporter may be produced, and the level of the RNA may provide a read-out for receptor activation. In this scenario, each receptor of interest may have its own RNA reporter that is unique to that receptor. Therefore, when multiple cell types, each expressing defined receptors (and their specific reporter), are mixed in a single well, the activation or inhibition of each receptor may be determined by the quantification of each unique RNA reporter.

The use of coded RNA-reporters allows layers of multiplexing. Specifically, because each cell population may be identified by the code included on the RNA expressed within that cells population, multiple populations of cells expressing distinct RNA reporters may be mixed together for exposure to ligands or other stimuli, including environmental conditions. In this way, individual cell populations that are affected by exposure to a given ligand may be identified. Moreover, sets of ligands capable of interacting with a given cell population, and modulators of these ligands, may be identified, and the ligands and/or modulators further characterized and studied for possible development into new drugs. In some embodiments, multiple cell populations may be exposed to multiple ligands simultaneously. Combinations of cell populations and ligands that display a ligand-mediated effect then may be studied individually. In other embodiments, multiple cell populations may be exposed to a library of agonists and antagonists. Those agonists and/or antagonists that interact with the cell populations are then identified and studied for possible drug discovery. In contrast, without the use of coded RNA reporters, different cell populations may need to be grown, treated, and analyzed in separate containers, such as in the individual wells of a microplate. Generally, the assays provided by the invention may involve any suitable number of reporters and cell types, including one, two, three, five, ten, one hundred, and/or one thousand, among others, depending on the assay, the desired results, and so on.

The use of coded RNA reporters described herein may apply to any cellular assay that results in a modulation of transcriptional activity, for example, any assay that currently uses a protein reporter. Each such assay may be multiplexed using RNA reporters. Thus, RNA-reporters may allow large scale multiplexing of reporter-based screens. Specifically, this may be of great value to pharmaceutical companies interested in screening compound libraries for biological effects on thousands of receptors.

The following sections describe further aspects of the invention, including (I) RNA reporters, (II) reporter genes, (III) introduction of reporter genes into cells, (IV) effectors, (V) introduction of effectors into cells, (VI) reporter cell libraries, (VII) modulators, and (VIII) measuring RNA reporter levels.

I. RNA Reporters

The RNA reporter generally comprises any polyribonucleotide species that may be transcribed in cells or tissues from a reporter gene template and that may be used to monitor the activity of an effector. In particular, the RNA reporter preferably comprises a polyribonucleotide species whose sequence may be determined independently of or in the absence of translation of the sequence to form a gene product. The polyribonucleotide species usually comprises a linear polymer formed of covalently linked ribonucleotide monomers selected from the group consisting of adenosine, cytidine, guanosine, inosine, uridine, and naturally occurring and synthetically modified derivatives thereof. The polynucleotide species may have any suitable length, including 2 to 500 nucleotides, preferably 2 to 100 nucleotides, and more preferably 30 to 70 nucleotides, among others.

An RNA reporter library generally comprises a set of two or more different RNA reporters, where each RNA reporter includes a sequence having at least one sequence feature that is chemically distinct from all other members of the RNA reporter library. This sequence feature may include one or more ribonucleotide monomer deletions, substitutions, or insertions within the sequence.

The various RNA reporters in a library may or may not be related to one another. For example, the RNA reporters may have common regions that are identical or substantially identical between species and variable regions that differ at one or more nucleotides positions between species. Alternatively, the RNA reporters may include no common region, for example, when completely distinct sequences are used in reporter genes. In either case, the RNA reporters may be chimeras comprising two or more sequence blocks.

The RNA reporters may include a code that is determined by nucleotide differences at one or more positions. Because RNA detection methods such as hybridization may be designed to differentiate between single nucleotide changes, as described below more fully, each nucleotide position within a sequence may contribute 4-fold possibilities (i.e., U, A, T, or C) to an RNA code. Therefore, the RNA code may be determined by n nucleotide positions within a sequence feature of an RNA reporter, with a total of $4^n$ possible distinguishable codes. In some cases, n may be the overall length of the RNA reporter. Although $4^n$ codes are possible, each RNA code may differ at plural nucleotide positions to facilitate distinguishing the RNA reporters. Generally, the greater the differences between different codes, the easier it is to distinguish the different codes. In some embodiments, a library of reporters may comprise a plurality of RNA codes that differ in sequence but that have substantially or identically the same length.

II. Reporter Genes

The reporter gene generally comprises any polynucleotide that includes (1) a regulatory region, and (2) a transcribed region encoding an RNA reporter. The regulatory region may include any control sequences that help to determine transcriptional initiation, elongation, and/or termination, and/or the speed of RNA reporter transcription. In turn, the control sequence may include a complex or simple enhancer, TATA box, initiator site, transcription factor binding elements, RNA structural determinants, and/or RNA polymerase or cofactor interaction sites, among others. Exemplary control sequences include promoters and promoter fragments from characterized genes and/or synthetic binding sites for regulated or constitutively active transcription factors, such as SP1, AP-1, NF-κB, and the like. Control sequences also may respond to a receptor class, such as G-protein coupled receptors (GPCRs, or "seven-pass transmembrane proteins"), interleukin receptors, and/or nuclear hormone receptors, among others.

A reporter gene may include any material capable of causing the appearance or production of a corresponding RNA reporter in a suitable cell. Suitable reporter genes may include DNA and/or RNA, and may be included in a viral vector or a shuttle vector capable of being propagated in bacteria or other nonvertebrate cells. The vector may include additional genes and control sequences to provide a selectable marker(s)/drug resistance, replication origin(s), effector expression, and the like. An exemplary reporter gene vector is a DNA plasmid with features that function in eukaryotic and prokaryotic cells.

Reporter genes that direct transcription of distinguishable RNA reporters may form a library of reporter genes. Control sequences within a reporter gene library may be identical or distinct. Each reporter gene in the library is a member, and the library may have two or more members.

A library of reporter genes with at least substantially identical regulatory regions may be produced by inserting a library of coded sequence features into a parental reporter gene. The sequence features thus may introduce a distinguishable RNA code into an otherwise identical reporter gene. For example, a library of synthetic sequence features, such as random or partially degenerate 20-mers, 50-mers, 100-mers, or other-mers, may be inserted into a site of the transcribed region of the parental reporter gene. Specific insertions may be cloned and sequenced for identification. The library, more generally, may have at least substantially identical regulatory regions if the sequences of the regulatory regions are at least substantially identical, and/or if the sequences do not differ by an amount that substantially affects or alters their regulatory function(s). Conversely, the library may have an at least substantially different regulatory region if the sequences of the regulatory regions are at least substantially different, and/or if the sequences differ by an amount that substantially affects or alters their regulatory function(s).

III. Introduction of Reporter Genes into Cells

Reporter genes from a reporter gene library may be introduced into one or more cells, tissues, or other transcriptional entities. The reporter genes may be introduced transiently, for example, by transfection, reverse transfection, electroporation, and/or infection. Alternatively, the reporter genes may be introduced stably to effect integration into the genome of the cell(s) or to allow extra-chromosomal maintenance, for example, by any of the techniques listed above. In some cases, the reporter genes may be introduced into different cell or tissue populations that include exogenously expressed effector proteins, as detailed more fully below.

Examples of cells and tissues that may be suitable for reporter gene introduction are described in U.S. patent application Ser. No. 10/120,900, filed Apr. 10, 2002, which is incorporated herein by reference in its entirety for all purposes.

IV. Effectors

The effector generally comprises any expressed biological material that regulates the expression of an RNA reporter from a reporter gene in a cell or tissue. Effectors may exert an effect on the reporter gene directly or indirectly. Effectors may function directly by binding to and/or functioning at a regulatory region of a reporter gene. Examples of direct effectors include nuclear hormone receptors (such as steroid receptors, retinoid receptors, retinoid X receptors, thyroid hormone receptors, and the like), NF-κB, AP-1, STAT factors, CREB, and other transcription factors. Effectors may function indirectly through signal transduction and/or second messenger pathways. Examples of indirect effectors include membrane receptors, such as GPCRs and receptor tyrosine kinases, and intracellular effectors, such as kinases, phosphatases, allosteric regulators, proteases, and the like.

V. Introduction of Effectors into Cells

The effector may be produced from endogenous and/or exogenous sequences. An endogenous sequence is native to a cell, whereas an exogenous sequence is introduced by cell manipulation. Exogenous sequences encoding effectors may be introduced by techniques similar to those outlined above for reporter gene introduction. Effector expression sequences may be introduced to cells concomitantly with reporter gene introduction, and may even be introduced on a common vector containing an effector sequence and a reporter gene. Alternatively, effector expression sequences may be introduced before and/or after reporter gene introduction. An exogenous effector may be expressed from a transiently or stably introduced sequence.

VI. Reporter Cell Libraries

The reporter cell library generally comprises a mixture of two or more cell populations that differ in reporter gene and in at least one additional aspect. The additional aspect may include the identity of the effector, and/or the identity and/or environment or modulator treatment of the cell population. Each cell population in the reporter cell library thus links the aspect to a coded reporter RNA. Other cell populations in the library that lack the aspect may serve as controls for the effect of the aspect, when they include a reporter gene with a similar or identical regulatory region.

VII. Modulators

The modulator generally comprises any material or treatment that a reporter cell library may be exposed to and that may alter the activity of a reporter gene. Modulators may include any drug, hormone, ligand, growth factor, growth inhibitor, or other agent or environmental condition. The modulator may act on a reporter gene indirectly through direct interaction with an effector or an effector partner. For example, the modulator may include an agonist or antagonist for effector signaling or activity. Alternatively, or in addition, the modulator may act on a reporter gene through direct effects on the reporter gene, a protein that binds to the reporter gene, and/or an indirect pathway.

Exemplary modulators, including drug candidates used to carry out a drug screen, are described in more detail in the patents and patent applications identified above under Cross-References and incorporated herein by reference, particularly U.S. patent application Ser. No. 10/120,900, filed Apr. 10, 2002.

VIII. Measuring RNA Reporter Levels

The presence, absence, and/or levels of RNA reporter levels may be measured using any suitable technique after producing a reporter cell library. For example, different reporter RNAs may be identified and quantified by hybridization between the different reporter RNAs and oligo- or polynucleotide identifier sequences that are substantially complementary to distinguishing sequence features of the reporter RNAs. If the distinguishing sequence features are relatively short and differ from one another by only one or a few nucleotide changes, the identifier sequences may be relatively short, and nonstringent hybridization conditions may be used. Alternatively, if the distinguishing sequence features are relatively long and less closely related to other reporter RNAs, the identifier sequences may be relatively long(er), and higher stringency hybridization conditions may be used.

RNA may be isolated from a reporter cell library for RNA reporter quantification. The isolated RNA then may be analyzed for content of each reporter RNA species by labeling the isolated RNA, followed by hybridization to positional and/or nonpositional arrays of identifier sequences. For example, the isolated RNA may be labeled by primed synthesis using primers and an optically detectable mononucleoside triphosphate derivative, such as a fluorescently tagged derivative. The labeled RNA then may be hybridized to a complementary identifier sequence (complementary to the newly synthesized strand), for example, a spatial array of identifier polynucleotides immobilized on a substrate. The strength of the optical signal at each array position may define a level of RNA reporter. Methods of making and using coded carriers to produce nonpositional arrays are described in more detail in the patents and patent applications identified above under Cross-References and incorporated herein by reference.

Some assays may employ additional indicator polynucleotides. For example, additional indicator polynucleotides, such as a housekeeping transcript encoding an actin, may be arrayed positionally or nonpositionally to provide a positive control for differences in RNA isolation and labeling efficiency, and to allow normalization between labeled RNA samples. Other indicator polynucleotides may be included to serve as negative controls. For example, nonsense polynucleotides, such as polynucleotides from unrelated species, may serve as negative controls. Furthermore, other indicator polynucleotides may be included in the array to measure adverse effects of a modulator or growth condition on the reporter cell library. For example, expression of genes transcriptionally regulated by stress, such as genes encoding stress-activated protein kinase and heat shock proteins, also may be used to measure general toxicity or negative effects of a modulator on cell health. Furthermore, expression of genes that specifically correlate with, or are involved in, detoxification pathways may be measured to determine modulator toxicity to cells.

In contrast to substrate hybridization, solution hybridization also may be used to quantify RNA reporter levels with isolated RNA. For example, RNAse protection assays may be used to measure levels of specific RNA reporters. Alternatively, hybridization may be carried out without any RNA isolation from cells. In this case, cells may be hybridized in situ with distinguishably labeled identifier probes that specifically hybridize with the reporter RNA species.

RNA reporter levels may be measured at one or more times after reporter genes are introduced into cells. For example, in some embodiments, steady state or endpoint RNA reporter levels may be measured. In other embodiments, kinetic values or transient changes may be measured during a time course following modulator exposure.

EXAMPLES

The following examples illustrate without limitation further aspects of the invention, including the use of RNA reporters to screen for modulators that are receptor-selective or -specific.

Example 1

This example, shown in FIG. 1, illustrates the use of a reporter cell library to measure the efficacy and specificity of a candidate receptor-modulator. A reporter cell library that includes three cell populations is illustrated schematically. Each cell population expresses, from a transfected plasmid expression vector, a distinct receptor (#1, #2, or #3) as effector. Each cell population also contains a reporter plasmid that directs the expression of a specific RNA reporter when the distinct receptor is activated. In this example, the reporter genes produce distinguishable RNA reporters at comparable low levels before modulator addition. RNA reporters are exemplified as including distinct sequence features GAC, GAA, and GCA. With addition of the modulator (compound X), the cell population expressing receptor #2 is shown to up-regulate the level of its reporter RNA (GAA).

To conduct a multiplexed analysis of RNA levels, RNA is extracted from the cell library, following treatment for a given amount of time with compound X. Extracted RNA is manipulated by standard techniques used for DNA microarrays and designed to analyze RNA expression profiles. The extracted RNA is used as a template for primed synthesis with reverse transcriptase to create a complementary probe mixture. The probe mixture is labeled during random-primed synthesis by incorporating a fluorescent nucleotide analog. In other examples, the RNA may be directly tagged, for example, with a terminal transferase enzyme.

The labeled probe mixture is hybridized to an immobilized array of identifier sequences. The identifier sequences correspond to housekeeping-gene transcripts for actin and each of the three reporter RNAs. The GAA identifier sequence provides a strong hybridization signal, corresponding to the increased level of GAA reporter RNA in the receptor #2 cell population. No detectable signals are provided by the GAC and GCA identifier sequences, suggesting that receptors #1 and #3 remain quiescent. The signal produced only by receptor #2 also indicates specificity for compound X action on receptor #2, relative to receptors #1 and #3. Furthermore, a detectable signal is present at the position of the actin sequence, providing a positive control signal ensuring that RNA isolation and manipulation occurred properly and also allowing normalization between different labeled RNA extracts.

Example 2

Figure 2:
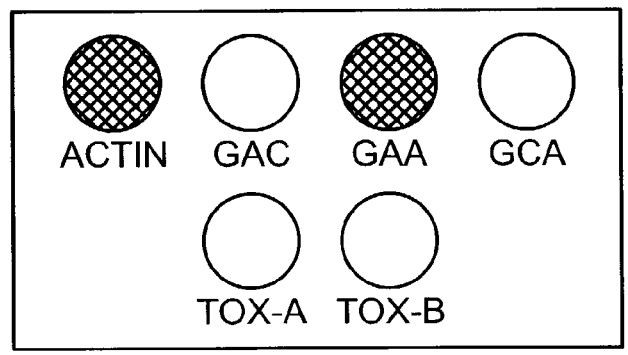
FIG. 2 is a schematic view of representative results from the analysis of FIG. 1, including measurement of the modulator's toxicity to cells.

This example, shown in FIG. 2, illustrates an expanded analysis with the labeled RNA from Example 1. In the expanded analysis, compound also is analyzed for a toxic effect on the reporter cell library. As shown, the identifier sequence array also includes identifier polynucleotides for Tox-A and Tox-B. Current methods for analyzing the toxic effects of compounds on cells are based on the regulation of the expression of genes involved in detoxification. Typically, this is done by the quantification of mRNA levels. Therefore, additional spots on the array may correspond to those genes (i.e., Tox-A and Tox-B) whose level correlates with compound toxicity. In the example of FIG. 1, not only is compound X specifically able to activate receptor 2, but compound X also likely is non-toxic due to the absence of any signal in the Tox-A and Tox-B spots.

Example 3

This example illustrates an exemplary assay involving small interfering RNAs (siRNAs). These RNAs are typically small (e.g., 20–25 base pair) double-stranded RNAs that may knock down or knock out the expression of gene(s) that are sufficiently homologous to either of the RNA strands in the duplex, in a phenomenon termed RNA interference (RNAi). In this assay, cells are transfected with one or more siRNAs (or antisense sequences and/or a complementary sense sequences), and RNA reporters as described herein are used to read out the effects of the siRNAs on multiple pathways. The siRNAs may be used alone, as sole modulators, or they may be used with one or more other compounds, for example, as described above, to identify the mechanism of action of the compounds.

Example 4

The invention provides improved assay systems for molecular pharmacology, including reverse molecular pharmacology, by providing encoded RNA reporter molecules that may be used to identify and/or characterize receptor ligands and/or modulators of receptor/ligand interactions. Additional aspects of reverse molecular pharmacology, and exemplary receptors and ligands that may be suitable for use with the invention are described in more detail in the patents and patent applications identified above under Cross-References and incorporated herein by reference, particularly U.S. patent application Ser. No. 10/120,908, filed Apr. 10, 2002.

The disclosure set forth above may encompass multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and nonobvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements. It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A method for multiplexed analysis of reporter gene activity, comprising:
    introducing a first reporter gene into a first cell population;
    introducing a second reporter gene into a second cell population, wherein the first and second reporter genes express distinguishable first and second RNA reporters, respectively; and
    measuring the levels of the first and second RNA reporters associated with the first and second cell populations, respectively.

2. The method of claim 1, further comprising isolating the first and second RNA reporters as a mixture from the first and second cell populations.

3. The method of claim 2, wherein the first and second cell populations are combined before isolating the first and second RNA reporters.

4. The method of claim 2, further comprising incubating the first and second cell populations prior to the steps of isolating and measuring to allow transcription of the first and second reporter genes.

5. The method of claim 1, wherein the first cell population expresses an exogenous first effector, and the second cell population expresses an exogenous second effector.

6. The method of claim 5, wherein the first and second effectors are both receptor proteins.

7. The method of claim 6, wherein the first and second effectors are both membrane-associated receptor proteins.

8. The method of claim 7, wherein the first and second effectors are both G-protein coupled receptor proteins.

9. The method of claim 6, wherein the first and second effectors are both nuclear receptor proteins.

10. The method of claim 6, wherein the first and second effectors are both receptor kinases.

11. The method of claim 1, wherein the first and second reporter RNAs have a common region and a distinguishing region.

12. The method of claim 11, wherein the distinguishing region includes between about 30 and 70 nucleotides.

13. The method of claim 1, wherein the first and second reporter genes have at least substantially identical regulatory regions.

14. The method of claim 1, wherein the first and second reporter genes have at least substantially different regulatory regions.

15. The method of claim 1, wherein the step of measuring the level of RNA reporters is carried out by hybridization to identifier sequences that include polynucleotide regions that are at least substantially complementary or at least substantially identical to the RNA reporters.

16. The method of claim 15, wherein at least some of the identifier sequences are associated with coded carriers in a nonpositional array.

17. The method of claim 15, further comprising labeling the isolated RNA reporters or a complementary transcript with a fluorescent tag, prior to the step of measuring.

18. The method of claim 17, further comprising illuminating the isolated RNA reporters or the complementary transcript with light capable of inducing fluorescence emission from the fluorescent tag, following the step of labeling.

19. The method of claim 1, further comprising exposing the first and second cell populations to a biological modulator, prior to the steps of isolating and measuring.

20. The method of claim 1, wherein the first and second reporter genes include distinguishing code regions having the same length but different nucleotide sequences.

21. The method of claim 1, further comprising introducing at least one small interfering RNA (siRNA) into at least one of the first and second cell populations, prior to the step of measuring.

22. The method of claim 1, further comprising:

introducing a third reporter gene into a third cell population, wherein the first, second, and third reporter genes express distinguishable first, second, and third RNA reporters, respectively; and measuring the level of the first, second, and third RNA reporters associated with the first, second, and third cell populations, respectively.

* * * * *